United States Patent
Bunce

[19]

[11] Patent Number: 5,853,670
[45] Date of Patent: Dec. 29, 1998

[54] LIQUID TRANSFER DEVICE FOR CONTROLLING LIQUID FLOW

[75] Inventor: Roger Abraham Bunce, Kings Norton, England

[73] Assignee: British Technology Group Limited, London, England

[21] Appl. No.: 637,724

[22] PCT Filed: Nov. 25, 1994

[86] PCT No.: PCT/GB94/02587

§ 371 Date: Apr. 30, 1996

§ 102(e) Date: Apr. 30, 1996

[87] PCT Pub. No.: WO95/14532

PCT Pub. Date: Jun. 1, 1995

[30] Foreign Application Priority Data

Nov. 26, 1993 [GB] United Kingdom ............ 9324310

[51] Int. Cl.[6] ........................................ G01N 33/48
[52] U.S. Cl. ............... 422/100; 422/58; 422/61
[58] Field of Search ............................ 422/58, 61

[56] References Cited

U.S. PATENT DOCUMENTS

| | | |
|---|---|---|
| 4,549,655 | 10/1985 | Forsythe, Jr. et al. . |
| 4,960,961 | 10/1990 | Gordon et al. .............. 422/58 |
| 5,135,873 | 8/1992 | Patel et al. . |
| 5,160,486 | 11/1992 | Schlipfenbacher et al. . |
| 5,198,193 | 3/1993 | Bunce et al. ............... 422/58 |
| 5,202,268 | 4/1993 | Kuhn et al. . |
| 5,230,966 | 7/1993 | Shartle et al. . |
| 5,240,862 | 8/1993 | Koenhen et al. . |
| 5,354,538 | 10/1994 | Bunce et al. ............... 422/58 |

FOREIGN PATENT DOCUMENTS

| | | |
|---|---|---|
| 0 418 765 A3 | 3/1991 | European Pat. Off. . |
| WO 90/11519 | 10/1990 | WIPO . |
| 92-15863 | 9/1992 | WIPO . |
| WO 93/11434 | 6/1993 | WIPO . |
| WO 93/23755 | 11/1993 | WIPO . |

OTHER PUBLICATIONS

Allen et al "A noninstrumented Quantitative test system and its application for determining cholesterol concentration in whole blood" Clin. Chem 36/9 1591–1597 (1990).

*Primary Examiner*—Lyle A. Alexander
*Attorney, Agent, or Firm*—Nixon & Vanderhye

[57] ABSTRACT

The invention relates to liquid transfer devices for use particularly in chemical diagnostic assays in extra-laboratory situations. The device comprises first and second capillary flow channels (210,212) in mutual abutment over an interface region (218), the first channel having a capillarity which is higher than that of the second channel. In a particular form, the first channel (210) defines a volume definition zone for a first liquid (223) in fluid connection with both the second channel (212) and means (219) for receiving excess first liquid, wherein the second channel is arranged for application of a second liquid (236). The first liquid may be a sample such as blood plasma, and the second liquid may be a liquid diluent. Use of the device allows the application of sample in excess, application of diluent liquid leading to reaction of assay reagents (228, 230) with sample in the volume definition zone only. A third channel (214) may be provided, of lower capillarity than that of the first channel (210), which may provide means by which liquid is introduced to the first channel, and/or means for receiving excess first liquid. The difference in capillarity between the channels may arise from differing pore sizes and/or wetting characteristics. Compression of material may be used to reduce pore size in the first channel and hence increase capillarity.

21 Claims, 5 Drawing Sheets

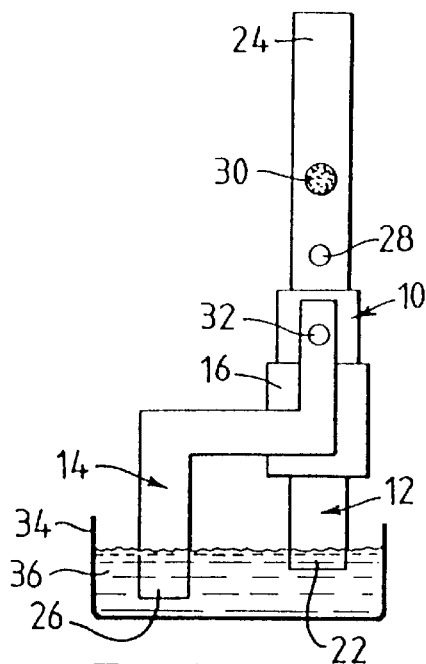
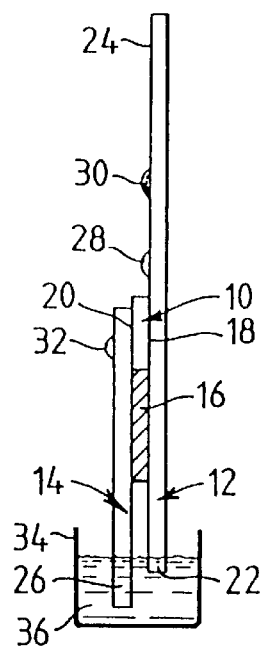
Fig. 1a    Fig. 1b
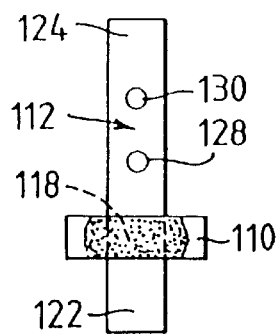
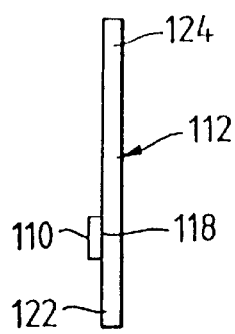
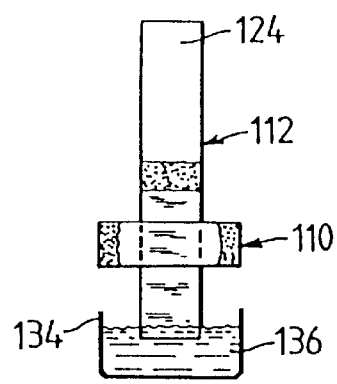
Fig. 2a    Fig. 2b    Fig. 2c
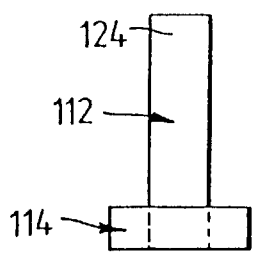
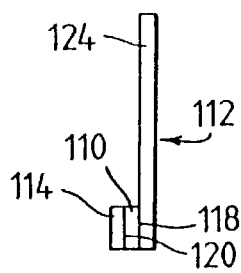
Fig. 3a    Fig. 3b

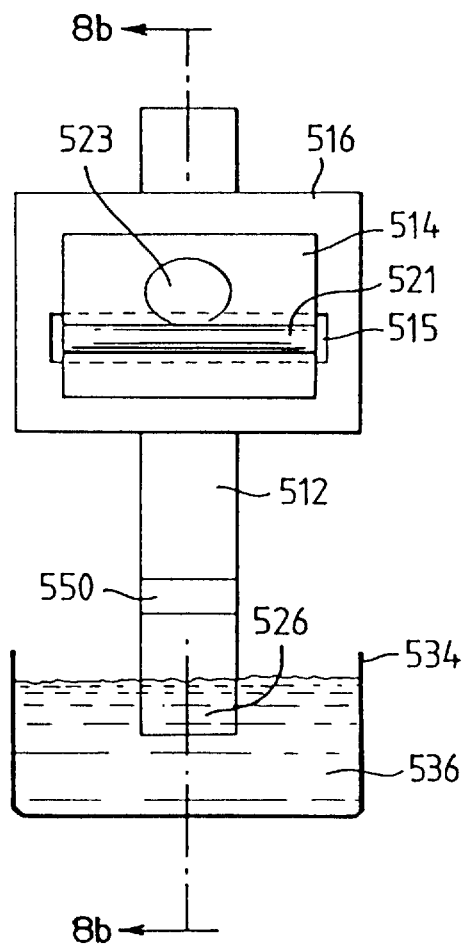 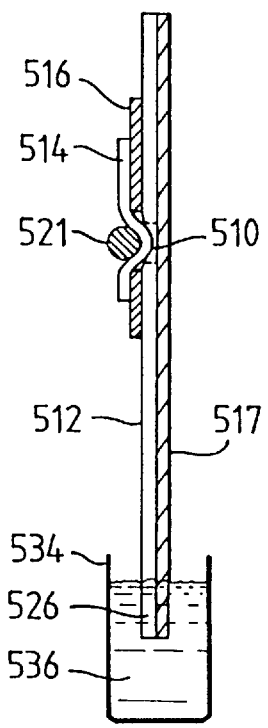
Fig. 8a
Fig. 8b

LIQUID TRANSFER DEVICE FOR CONTROLLING LIQUID FLOW

This invention relates to a liquid transfer device particularly, but not exclusively, for liquid sequencing, timing and volume metering in chemical diagnostic assays in extra-laboratory situations.

BACKGROUND OF THE INVENTION

Various liquid transfer devices have been proposed and designed to avoid any need for complex procedures, so as to be suitable for use by relatively inexperienced persons. In some assays, it is necessary for there to be a timed sequence of reagent additions to an analyte, and devices have been previously proposed to deliver such reagents automatically and sequentially by the use of multiple capillary flow channels. Examples of capillary flow diagnostic devices are described, for example, in GB-A-2231150 and corresponding WO90/11519. Sequential delivery of reagents in such devices is achieved by forming the flow channels of different effective lengths so that the reagent which is in the flow channel of longer effective length is delivered later than the reagent in the flow channel of shorter effective length. However, this can lead to a relatively bulky device.

GB-A-2231150 also discloses various diagnostic devices which include an expanding foam which is intended to connect the flow channels together automatically after a predetermined time. However, it is not always easy to arrange the foam to expand reproducibly, either due to material properties, or interfacial connection or circuit configuration.

It has also been proposed by M. P. Allen et al, Clinical Chemistry 36 (1990), 1591 to provide a manually operable valve mechanism for shearing off a defined volume of sample into a liquid transfer device so as to ensure that a relatively accurate sample volume is used, thereby to reduce the possibility of error. However, the mechanism is manually operated and involves the use of precision moving parts which are relatively expensive to manufacture.

U.S. Pat. No. 5,240,862 discloses a device incorporating a red cell separation membrane in temporary contact with a sample collection membrane of known volumetric capacity. In use, whole blood is applied to the separation membrane which separates and applies serum to the collection membrane. The separation membrane containing red cells and excess plasma is manually removed from the collection membrane and discarded. The defined volume of the plasma contained in the collection membrane is then eluted out and analysed. Here again, a manual procedure is involved, and the separation membrane needs to be disposed of safely.

EP-A-0 418 765 describes a test device with flow control means constituted by a hydrophilic membrane in contact with a hydrophobic membrane. The hydrophilic membrane is accessible by way of a port such that an assay liquid may be applied to it. Once analyte present has bound to the hydrophilic membrane, further flow into the hydrophobic membrane can be initiated by applying a wetting agent. The device described offers no means to define the volume of the applied assay liquid, and if such liquid is applied in excess it will almost certainly tend to pass into the hydrophobic layer before the intended time, due to saturation of the pores. The procedure involved requires further intervention by a user who must apply the wetting agent at the correct time to the first channel as there is no way of accessing the hydrophobic membrane to apply any liquid to it.

SUMMARY OF THE INVENTION

WO-92/15863 teaches a test strip device comprising a wicking architecture within an impermeable housing. The device includes an application site accessible through a port, and applied sample, or a part thereof, can travel to an analysis site where a reagent causes a detectable change observable through a second port. The flow control means may include a glass fleece to separate red blood cells from whole blood. The application site is in flow connection with a peripheral sink, such that in operation excess sample is carried away from the operative site. Sample applied to the application site can immediately pass into the next layer before the sink has been able to accomplish any degree of volume definition, and hence there is the danger that sample can reach the reagent site in an undesirably large volume. There is thus no 'holding function' afforded by the device.

U.S. Pat. No. 4,960,691 and WO-90/11519 (referred to above) both teach porous flow test strip devices. In each case, reagents and/or sample can be transported by a solvent through the device for sequential reactions. However, materials are simply deposited on, or applied to, the test strip directly and no specific features addressed to volume definition are considered.

WO 93/11434 describes a sample collection device with means to indicate whether sufficient sample has been applied.

U.S. Pat. No. 5,202,268 describes a composite porous flow test device, wherein a specific sequence of interconnected zones of differing capillarity ensure that sample liquid follows a predetermined pathway and so encounters the correct reaction sites. Flow is promoted simply by the application of the sample, as the device is configured such that the various zones 'push' and 'pull' the sample along its prescribed path. There is no provision for dealing with excess sample.

WO-93/23755 teaches an assay device having two contiguous material zones of different porosities to guide the flow of an applied sample and/or a washing agent. The first material (to which the sample is applied) may be either of a lower or a higher porosity than the second material. No automatic volume definition is possible. When a washing step is employed, the second material acts purely as a waste reservoir to absorb the large volumes of washing agent.

It is an object of the present invention to provide an improved liquid transfer device which, in various embodiments, can obviate or mitigate the disadvantages of the previously proposed devices.

According to the present invention, there is provided a liquid transfer device for controlling liquid flow, comprising first and second capillary flow channels, the first and second channels being in mutual abutment over an interface region, and the first channel having a capillarity towards the liquid which is higher than that of the second channel, the first channel defining a volume definition zone for a first liquid to be applied, the volume definition zone being in fluid connection with the second channel by way of the interface region, characterised in that the volume definition zone is also in fluid connection with means for receiving excess first liquid, and that the second channel is arranged for application of a second liquid other than by way of the first channel.

This difference in capillarity may be obtained by forming the channels from materials having (a) different pore sizes and/or (b) different wetting characteristics with respect to the liquid. Alternatively, selected area(s) of the channel may be modified to alter the capillarity in such area(s) by compressing or by selectively removing material.

In the devices of the present invention, the liquid will not flow from the first channel (having the higher capillarity) to the second channel (having the lower capillarity) when there is no liquid in the interface region of the second channel and when the first channel is unsaturated with liquid, but such flow can be initiated by wetting the second channel at the interface region and/or by saturating the first channel with liquid, at least in the interface region. This effect can be used to control the flow of liquid in the device in order to produce a variety of useful effects.

The liquid whose flow is to be controlled will typically comprise an individual chemical reagent, a diluent, or an applied sample or constituent part thereof. The term 'liquid', in this specification and claims, embraces any substances which can be transported by capillary flow, including solutions or compositions containing particulate matter.

Such a device can be employed for passing a relatively accurate quantity of material applied to the first channel through to the second channel. According to this aspect of the invention the first channel of the device defines a volume definition zone for a first liquid, this zone being in fluid connection with (a) the second channel and with (b) a means for receiving excess first liquid, and wherein the second channel is arranged for application of a second liquid.

Typically, the first liquid may be an applied sample suspected of containing analyte of interest, such as blood or blood plasma, and the second liquid may be a diluent, such as an appropriate buffer solution. The second liquid may be applied directly to the second channel, or may be applied via the first channel so as to wet the interface between the first and second channels. In this latter case, it is the addition of the second liquid to an already wetted channel which causes saturation at the interface and thereby drives the first liquid into the previously dry second channel.

If a sample is applied to the first channel in a quantity which exceeds that which is to be supplied to the second channel (but which is not in an amount sufficient to saturate the first channel completely), then such quantity of sample will distribute itself quickly throughout the first channel including the interface region between the first and second channels, but none of the sample will be transferred to the second channel when the latter is dry in said interface region. Excess sample is accommodated by the means for receiving excess first liquid. When diluent liquid is caused to flow along the second channel and the interface region becomes wetted, then only that volume of the sample which is at the interface region of the first channel will be transferred to the second channel, the remainder of the sample being retained.

Preferably, the second channel and the means for receiving excess first liquid are connected only via the first channel. To this purpose, a liquid impermeable barrier is provided between the second channel and the means for receiving excess first liquid, and this may take the form of an airgap or an impervious membrane.

In one form of the invention, the means for receiving excess first liquid is a part of the first channel distant from said volume definition zone. To this end, the first channel may feature one or more lateral portions spaced from the interface region to act as a waste reservoir. More generally, the interface region between the first and second channels is disposed away from at least one end (and preferably both ends) of each of the first and second channels.

Preferably, a third capillary flow channel is provided in fluid connection with the first channel, having a capillarity towards the liquid which is lower than that of the first channel. Where a third channel is provided, the first channel may be employed to prevent flow of liquid from the second channel to the third channel under certain conditions. The third channel may provide the means for receiving excess first liquid. In addition or alternatively, the third channel may comprise means by which first liquid is introduced to the first channel. In this way, sample can be applied to the first channel via the route of the third channel, only the defined volume passing into the first channel, and the excess being retained by the third channel.

The third channel may comprise a means for separating and retaining selected matter, and for blood tests it may take the form of a blood separation membrane for retaining red blood cells contained in whole blood, whilst allowing passage of blood plasma.

The difference in capillarity between the various channels may be obtained by forming the channels from materials having differing pore sizes and/or wetting characteristics. The channels may be fabricated from different materials, or may be chemically treated after manufacture to exhibit different properties. Alternatively, the difference in capillarity between channels may be obtained by modifying the capillarity of at least one channel by compressing or by selectively removing material.

With regard to this last aspect, in a preferred form the device includes a compression member of appropriate form to selectively compress capillary flow material thereby to form said first channel. This compression has the effect of decreasing pore size and hence increasing capillarity. When the flow channels are contained in a housing, the compression member can be formed as a part of the housing. Additionally, the housing may be provided with first liquid application means associated with the compression member.

For multiple simultaneous assays, material may be compressed in a number of discrete areas to create multiple volume definition zones.

In a modification of the invention, the third channel referred to above may be provided so as to overlie and engage the first channel on the opposite side thereof to the second channel. With such an arrangement, a sample to be metered into the second channel can be applied to the third channel followed by application of liquid diluent so that the sample becomes distributed before passing through to the first channel having a higher capillarity. After the sample has entered the first channel and has become distributed therein, the liquid diluent saturates the first channel and causes the required volume of sample to pass through to the second channel. The advantage of providing the third channel is to avoid the risk of local saturation of the first channel at the interface region between the first and second channels when the sample is first applied. Such a condition could exist if the sample is applied too quickly directly to the first channel at the intermediate interface region.

In this last embodiment, the first, second and third channels can be arranged in a stack with the first channel being physically sandwiched between the second and third channels at least at the interface regions thereof. It is also within the scope of the invention for the second and third channels to be substantially coplanar and be bridged by the first channel which may have a portion extending away from the volume definition zone to provide the means for receiving first liquid in excess of the amount to be transferred to the second channel.

The device may comprise indicator means to give an indication to a user whether or not sufficient first liquid has been applied to the volume definition zone. Such indicator means may comprise a compressed region of one of the channels provided with a visible marker dye able to be entrained in liquid flow.

Additionally, the device may include a tubular capillary flow channel in fluid connection with the means for receiving excess first liquid, to provide a flow path for such excess.

In an alternative embodiment of the invention, the second and third channels have respective ends distant from their respective interface regions with the first channel and are arranged such that, if liquid is applied simultaneously to their ends, it is delivered at different times to the respective interface regions. This form of device may be used to provide enhanced control of liquid flow in the case of timed sequence reagent additions to an analyte.

In one form of this last embodiment, the first, second and third channels form part of an assay device for an antigen in a sample being assayed. In such a device, it is preferred for the second channel to have first and second sites spaced apart longitudinally of the second channel on an opposite side of the interface region between the first and second channels from a liquid supply end of the second channel, the first site being disposed between said interface region and said second site and containing a first reagent, and the third channel having (a) a liquid supply end spaced from the interface region between the first and third channels, and (b) a reagent site disposed between the liquid supply end of the third channel and the first channel. With such an arrangement, liquid flowing from the liquid supply end of the second channel can flow into the first channel and can also flow towards the first and second sites but cannot flow between the first channel and the third channel until the latter has been wetted at the interface region between the first and third channels by liquid which has been supplied from the liquid supply end of the third channel (assuming that the first channel is not saturated). Such a device can be used, for example, where the reagent at the first site is an enzyme-labelled antibody to the antigen being assayed for in the sample, the reagent at the reagent site in the third channel is a reagent which enables visualisation of the enzyme, and the second site has an antibody which is capable of binding to the antigen of interest which may be present in the sample.

The present invention is also directed to a method of operating a liquid transfer device comprising:

providing first and second capillary flow channels in mutual abutment over an interface region, the first channel having a higher capillarity than that of the second channel and defining a first liquid retention volume, characterised by the steps of:

providing means for receiving excess first liquid in fluid communication with said first liquid retention volume;

applying to said first channel first liquid in a volume at least as great as said retention volume, said first liquid being prevented from crossing said interface region by virtue of the differential capillarity thereacross, any excess first liquid passing to said means for receiving excess first liquid; and applying second liquid to the device other than by way of the first channel, so as to wet the interface region between the first and second channels such that the first liquid can cross the interface region in a defined volume for subsequent transport in the flow of said second liquid.

BRIEF DESCRIPTION OF THE DRAWINGS

Embodiments of the present invention will now be described, by way of non-limiting example only, with reference to the accompanying drawings, in which:

FIGS. 1a and 1b are schematic front and side elevations respectively of one embodiment of a liquid transfer device according to the present invention;

FIGS. 2a, 2b and 2c are schematic front, side and front (in use) elevations of a second embodiment of a liquid transfer device according to the present invention;

FIGS. 3a and 3b are front and side elevations of a modified device similar to that of FIGS. 2a and 2b;

FIGS. 5, 6, 7, 8a, 8b, 9, 10 and 11 illustrate yet further embodiments of devices according to the invention.

DETAILED DESCRIPTION OF PREFERRED EMBODIMENTS

Figure 4A:
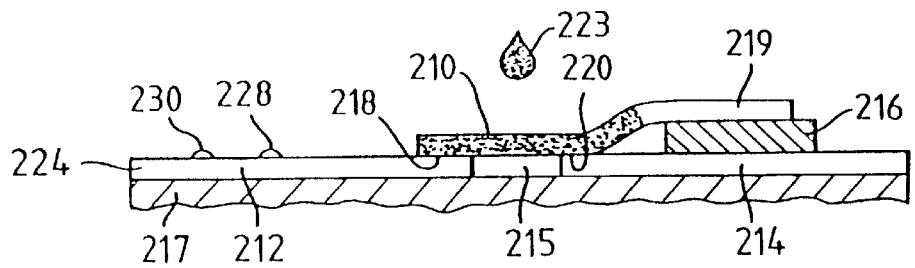
FIGS. 4a, 4b, 4c, 4d and 4e are views showing a third embodiment of liquid transfer device at various stages in the use thereof during an assay.
Figure 4B:
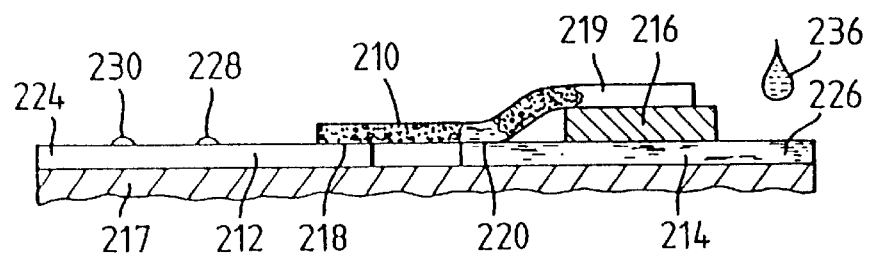
Figure 4C:
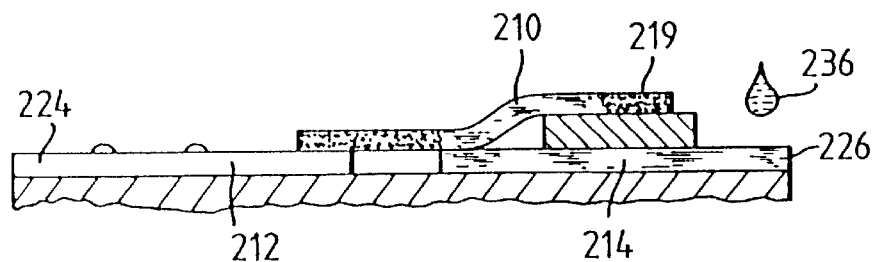

Referring now to FIGS. 1a and 1b of the drawings, the liquid transfer device comprises first, second and third capillary flow channels 10,12 and 14, respectively. The first channel 10 is formed of a porous material having a smaller pore size than the second and third channels 12 and 14. In this embodiment, the first channel 10 is formed of a 12 $\mu$m nitrocellulose membrane (available from Scheicher and Schuell), whilst the second and third channels 12 and 14 are formed of AP25 [Trademark] glass fibre-based filter paper (available from Millipore Limited). Thus, the first channel 10 has a higher capillarity than the second and third channels 12 and 14. The channels 10 to 14 are held together either by clamping means incorporated into a housing (not shown) of the device and/or by use of an adhesive which is provided on only selected localised regions of the various parts (e.g. in a pattern as disclosed in GB-A-2231150). An impervious membrane 16 serves to separate the second and third channels 12 and 14. The channels 10 to 14 are secured together so that the first and second channels 10 and 12 are in mutual abutment over an interface region 18, whilst the first and third channels 10 and 14 are in mutual abutment over an interface region 20 spaced from the region 18 (see FIG. 1b).

The interface region 18 is provided intermediate a liquid diluent supply end 22 and a waste end region 24 of the second channel 12. The interface region 20 is provided at an end of the third channel 14 which is opposite to a liquid diluent supply end 26 thereof. As can be seen from FIG. 1a, the second channel 12 is linear whilst the third channel 14 is cranked so that the effective length of the third channel 14 between the liquid diluent supply end 26 and the interface region 20 is greater than the effective length of the first channel between the liquid diluent supply end 22 and the interface region 18. It will also be apparent from FIGS. 1a and 1b that, in the illustrated orientation of the device, the liquid diluent supply end 26 is disposed below the liquid diluent supply end 22.

At a first site 28 on the second channel 12 between the interface region 18 and the waste end region 24, there is provided an enzyme-labelled immobilised antibody which is capable of binding with an antigen of interest which may be present in a sample to be subjected to an immunoassay in the device.

At a second site 30, which is disposed on the second channel 12 between the first site 28 and the waste end region 24, there is provided an antibody which is capable of binding to the antigen of interest.

At a third site 32, there is dried onto the third channel 14, a calorimetric substrate to the enzyme provided at the first site 28, such substrate being soluble and free to flow with liquid diluent. The third site 32 is provided in the third channel 14 adjacent the interface region 20.

In use, the sample to be subjected to the enzyme immunoassay is applied to the second site 30. If the antigen of interest is present in the sample, it binds to the antibody immobilised onto the second channel 12 at the second site 30. The liquid diluent supply ends 22 and 26 of the channels 12 and 14, respectively, are then immersed in a shallow reservoir 34 containing a quantity of the liquid diluent 36. The diluent 36 quickly flows along the second channel 12 by capillary action. When it reaches the interface region 18, it passes into the first channel 10 but does not actually saturate the latter because it is free to continue to flow along the second channel 12 beyond the interface region 18 and towards the first and second sites 28 and 30 and the waste end region 24. The liquid diluent in the first channel 10 is not, however, capable of passing into the third channel 14 via the interface region 20 because the channel 14 is formed of a larger pore material and because, at this stage, it is dry at the interface region 20.

The liquid diluent continues to flow along the second channel 12 so as to reconstitute the enzyme-labelled antibody at the first site 28 and move it to the second site 30 where it binds with any antigen from the sample which has been bound to the antibody at the second site 30. Thus, any antigen present in the sample starts to be labelled with enzyme. The time for the liquid diluent to flow along the second channel 12 provides incubation timing of any antigen in the sample with immobilised antibody at the second site 30. By this time, the level of liquid diluent 36 in the reservoir 34 has dropped to below the liquid supply end 22 of the second channel 12 so that flow in the latter stops and the enzyme-labelled antibody remains substantially stationary and incubates with any antigen present at the second site 30.

Meanwhile, liquid diluent passes from the liquid supply end 26 along the third channel 14 by capillary action, the effective length of the third channel 14 being arranged so as automatically to time the incubations occurring in the second channel 12. When the liquid diluent reaches the end of the third channel 14, it passes from the latter into the first channel 10 through the interface region 20, this being possible because the pore size of the first channel 10 is smaller than that of the third channel 14.

Thus, all of the channels 10, 12 and 14 are wetted in the interface regions 18 and 20 so that flow of liquid diluent is effectively switched completely on. Thereafter, liquid diluent flows along the third channel 14 through the first channel 10 and into the second channel 12 and from there towards the first and second sites 28 and 30 to the waste end region 24 which, at this stage, has not yet become saturated. Initially, such flow of liquid diluent provides a wash step to remove any unbound material at the second site 30. Further flow transports the calorimetric substrate from the third site 32 to the second site 30 where, if enzyme is present, an insoluble coloured product is formed. Further flow in the second channel 12 serves to provide a final wash which terminates when the waste end region 24 is saturated or when the level of liquid diluent 36 in the reservoir 34 drops below the supply end 26 of the third channel 14.

Referring now to FIGS. 2a to 2c of the drawings, the liquid transfer device illustrated therein is for sample volume metering. In this device, parts which are similar to those of the device of FIGS. 1a and 1b are accorded the same reference numerals but in the 100 series. In this device, first channel 110 having a higher capillarity than second channel 112 may be formed of 12 μm nitrocellulose or blood separation membrane PS21 [Trademark] (obtainable from Prime Care/X-Flow B.V.) of the type described in U.S. Pat. No. 5,240,862. The second channel 112 is typically formed of AP25 [Trademark].

The first and second channels 110 and 112 are arranged in cruciform juxtaposition and may be held together in any of the ways described hereinabove in relation to FIGS. 1a and 1b so that interface region 118 is disposed intermediate the ends of both channels 110 and 112. In use, a volume of blood plasma (or whole blood if a red cell separation membrane is used as the first channel 110) is applied centrally to the first channel 110 in an amount which exceeds the volume required for an immunoassay to be conducted in first channel 112 but which is insufficient to saturate the first channel 110. The plasma or blood applied centrally to the first channel 110 passes symmetrically towards the ends of the first channel 110 and does not pass through the interface region 118 into the second channel 112 because the latter is dry at this stage.

Liquid diluent supply end 122 of the second channel 112 is then immersed into liquid diluent 136 in reservoir 134 (FIG. 2c). This causes liquid diluent to pass alone the second channel 112 so that it wets the latter at the interface region 118. In this condition, liquid flow can occur from the first channel 110 to the second channel 112. Thus, a substantially predetermined volume of the central region of the sample applied to the first channel 110 is transferred into the channel 112 and excess sample material is diverted towards the free ends of the first channel 110. Further flow along the second channel 112 causes the predetermined sample volume to flow along the channel towards the waste end region 124 and through one or more sites (typically shown by reference numerals 128 and 130) which include analyte testing means. For example, such analyte testing means may include labelling the analyte of interest, if present, with antibody-coated gold sol or latex particles. Subsequent immobilisation of such particles onto a porous media support provides visual indication of the presence or otherwise of analyte in the sample.

In the modified device of FIGS. 3a and 3b, third channel 114 is co-extensive with the first channel 110 and is in complete facial abutment therewith so that interface region 120 extends over the entire length of each channel 110 and 114. In this embodiment, the second channel 112 extends only on one side of the first channel 110 because the second channel 112 is arranged to be supplied with liquid diluent drop-wise from a pipette rather than by immersing part of the channel 112 into diluent contained in a reservoir. The third channel 114 is an optional but preferred addition since it acts as a spreading layer and prevents localised saturation of the first channel 110 which would otherwise cause the sample to pass prematurely through the interface region 118 into the second channel 110.

In use of the device of FIGS. 3a and 3b, the sample is slowly applied centrally to the third channel 114 and diluent is then applied drop-wise from a pipette centrally onto the same channel 114. The addition of this extra liquid to an already wetted first channel 110 causes flow through the interface region 118 into the second channel 112. Hence, a substantially predetermined volume of the central region of the sample is transferred from the first channel 110 into the second channel 112 for assay described hereinabove in relation to FIGS. 2a and 2c.

Referring now to FIGS. 4a to 4e, there is illustrated a sample volume metering device which is particularly amenable to mass production. This is because the device can be assembled in the form of a rectangular sheet and then cut up to form individual analytical strips. The device illustrated in FIGS. 4a to 4e also mitigates possible problems caused by elongation and imprecision of sample metering in cases where diluent flows partly through the second channel 112 and partly through the first channel 110 (see FIGS. 2 and 3).

In FIGS. 4a to 4e, the parts similar to those of the previous devices are accorded the same reference numerals but in the 200 series. In this device, second and third channels 212 and 214 are separated by a gap 215 and mounted on a rigid impermeable support 217 so that the channels 212 and 214 are coplanar. First channel 210 bridges the gap 215 and is in abutment with the second and third channels 212 and 214 via respective interface regions 218 and 220. As can be seen in the drawing, interface region 218 is provided at one end of the first channel 210, whilst the opposite end defines a waste reservoir 219 separated from the third channel 214 by impervious membrane 216. Like the previous embodiments, the second channel 212 is provided with analyte testing means, typically provided at sites 228 and 230, and also with waste region 224 remote from interface region 218.

In use, an undefined but appropriate volume of blood, serum or other liquid or semi-liquid, sample 223 (see FIG. 4a) is applied to the first channel 210 in the region of the gap 215. The composition of the first channel 210 is chosen to suit the particular type of sample used.

The volume of the sample, for effective use of the device, is chosen so that it covers an area between and including the interface regions 218 and 220, and up to an area between the interface region 220 and almost to the end of the first channel 210 at the waste reservoir 219. In other words, the size of the reservoir region 219 is chosen to allow the device to tolerate the expected sample volume variation.

Liquid diluent 236 is then added to end region 226 of the third channel 214 using either a pipette (as shown) or a diluent reservoir (see FIG. 2c). Diluent passes along the third channel 214, through the interface region 220 and into the first channel 210 because liquid, sample 223 (see FIG. 4a) is applied to the first channel 210 in the region of the gap 215. The composition of the first channel 210 is chosen to suit the particular type of sample used.

The volume of the sample, for effective use of the device, is chosen so that it covers an area between and including the interface regions 218 and 220, and up to an area between the interface region 220 and almost to the end of the first channel 210 at the waste reservoir 219. In other words, the size of the reservoir region 219 is chosen to allow the device to tolerate the expected sample volume variation.

Figure 4D:
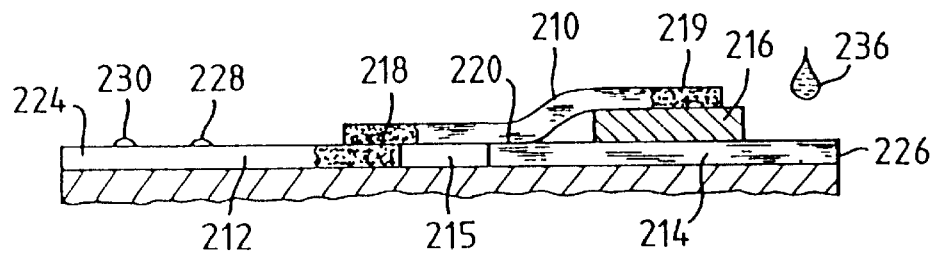
Figure 4E:
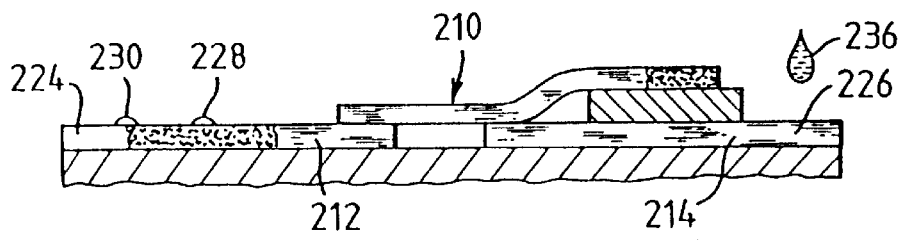

Liquid diluent 236 is then added to end region 226 of the third channel 214 using either a pipette (as shown) or a diluent reservoir (see FIG. 2c). Diluent passes along the third channel 214, through the interface region 220 and into the first channel 210 because the pore size in the first channel 210 is smaller than that in the third channel 214 (see FIG. 4b). Hence, the volume of the sample to be used for subsequent analysis is defined by that volume of the sample which lies within the first channel between the interface regions 220 and 218. Diluent from the third channel 214 continuing to flow into the first channel 210 drives excess sample into the reservoir region 219 (see FIG. 4c). During this time, the sample cannot flow across interface region 218 into the second channel 212 because the pores in the first channel 210 are smaller than those in the second channel 212. Only when channel 210 is totally saturated can sample begin to flow across the interface region 218 into the second channel 212 (FIG. 4d). This is then followed by flow of diluent into the second channel 212 (FIG. 4e).

The reservoir 219 is arranged to form a flow stagnation region and therefore excess sample contained therein cannot ingress into the second channel 212 and affect the assay. Hence, a predetermined sample volume, followed by diluent, flows along the second channel 212 to the analyte testing means 228 and 230. Alternatively, the second channel 212 together with the sample and diluent contained therein may be removed and analysed separately.

A modification (not illustrated) to the 'bridge' form channel arrangement of FIG. 4 for use with a blood sample employs a blood separation membrane such as PS21 to provide the first channel 210, such that when whole blood is provided to the separator membrane, blood plasma only arrives at the interface with the second channel for subsequent volume definition, the defined volume passing into the second 212 after diluent application. The device may include an indicator such as colloidal gold labelled antibody provided at the interface region 218, the liquid diluent therefore carrying a mixture of serum and gold along the second channel 212 for subsequent analysis. This device has been the subject of experimental validation in application to a myoglobin assay, where satisfactory sample volume definition and analysis was achieved in laboratory conditions.

The blood separation membrane affords the means of providing the sample excess reservoir region 219, as well as the route by which the sample is applied to the first channel.

Figure 5:
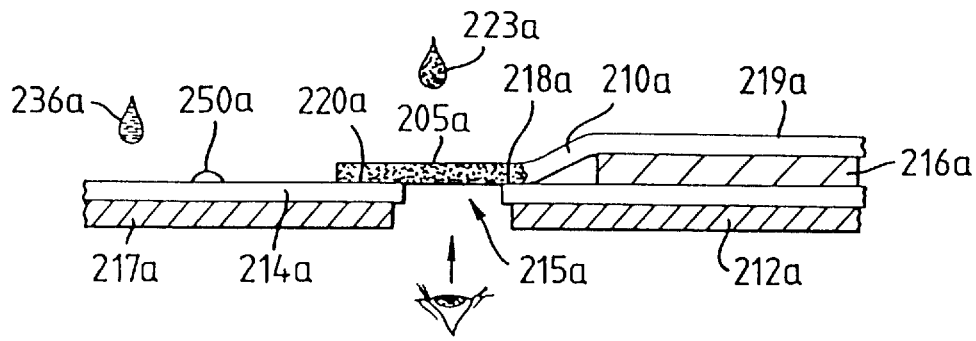

Referring now to FIG. 5, the liquid transfer device illustrated therein is also applicable to sample volume metering and also uses a 'bridge' form channel arrangement. However, in this case the device is designed to include analyte testing means in the vicinity of the sample application site, such that subsequent liquid transport to reaction sites is not required. The same reference numerals to those used in FIG. 4 are used to indicate similar components, with the addition in each case of suffix 'a'.

In this form, the device features a viewing port as shown in the rigid support or housing 217a, coincident with the gap 215a between second and third channels 212a and 214a. The first channel 210a, of smaller pore size, is provided with immobilised antibody to the analyte of interest extending over a certain area, denoted by numeral 205a. whilst channel 214a incorporates colloidal gold labelled antibody 250a.

In use, an undefined but appropriate volume of blood serum 223a is applied to the first channel 210a to extend from interface regions 218a to 220a and further towards the waste region 219a, therefore filling a region larger than the immobilised antibody area 205a. Sample cannot flow into channel 212a or 214a due to the lower capillarity of those channels, but remains in channel 210a where any antigen present in the serum binds to the immobilised antibody.

Diluent liquid 236a is then added to the end region 226a of the third channel 214a. and this passes alone the channel through interface region 220a and into the first channel 210a, carrying the gold 250a at its flow front. If the analyte of interest is present it will be labelled with gold and the indicated result viewed through aperture 215a. It will be appreciated that unlike the device of FIG. 4, the sample in channel 210a is not divided between that passing into the second channel and that being driven into the waste reservoir. Instead, the device ensures that an undefined sample volume can be applied, but only a specific defined volume can interact with immobilised antibody in region 205a, due to the fact that additional sample cannot pass into channel 214a, then to be transported back into channel 210a by the diluent flow to interact with the immobilised antibody at 205a.

Figure 6:
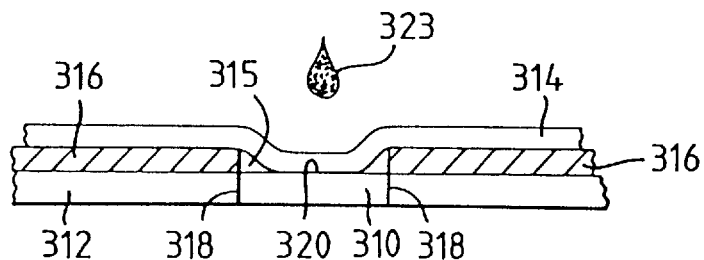

The above embodiments of the invention employ overlying, initially separate channels of strip-form porous material, an interface region being formed in the region where one channel overlies another. An alternative to this arrangement is shown in FIG. 6 which illustrates a further sample volume metering device, the parts similar to those of the previous devices being accorded the same reference numerals but in the 300 series.

In this device, first channel 310 and second channel 312 are arranged in the common plane of a strip device, channel 310 comprising a piece of small pore (high capillary) material inserted and fixed into a complementary gap in channel 312 of lower capillarity material. The interface region 318 is then formed by the connection between the mutually abutting side faces of the respective channels. The device illustrated includes a third channel 314 overlying the first channel 310 and being held in flow contact with the first channel at an interface 320 by appropriate means which may be, for example, part of a shaped housing. The third channel 314 in this case is a blood separation membrane such as PS21. In use of such a material, as explained earlier in this specification, whole blood may be applied to one surface of the membrane, blood plasma only passing through the membrane, the red cells being retained within the membrane material. Aside from acting as a blood separation membrane, channel 314 provides a reservoir means to accommodate excess sample. An impervious membrane 316 is positioned between the second and third channels to prevent flow contact therebetween and thereby to avoid the possibility of sample flooding into the second channel if localised saturation occurs in the third channel. Gap 315 in the impervious membrane is suitably sized and shaped to afford the required flow contact between the third and first channels.

In use, an undefined but appropriate volume of whole blood, sample 323, is applied to the third channel 314 in the vicinity of interface 320. The appropriate volume is less than that volume which would saturate the separation membrane. The blood plasma passes from the underside of channel 314 into first channel 310, in which it is retained due to the fact that it will not pass through the interface region 318 into the lower-capillarity second channel 312 whilst the latter is unwetted. Channel 310 therefore acts as a sample volume definition zone, whilst channel 314 acts to define means for receiving excess sample.

Liquid diluent is then introduced at one end (not shown) of second channel 312 by way of a pipette or a diluent reservoir. Diluent passes along the channel, across the interface region 318, and into the first channel 310. On wetting the second channel in the interface region, this flow is able to carry the defined volume of sample retained within first channel 310 downstream into and through the second channel 312, for subsequent analysis at reagent/detection sites incoporated therein.

It is shown by experimentation that, in use of the device, there is negligible flow of the defined sample and diluent into the separation membrane from the first channel due to the high resistance to flow. It is to be noted that in devices of this type using a blood separation membrane, the sample volume defined in the first channel is completely independent of the haematocrit of blood, provided that the whole blood sample contains sufficient plasma to fill the first channel 310.

Figure 7:
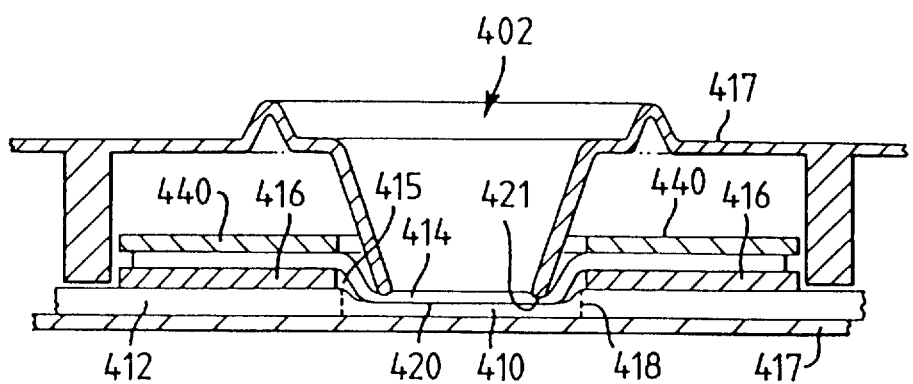

FIG. 7 shows an improvement to the device of FIG. 6 making use of an area of compressed material to form the first, higher capillarity, channel within the second channel, a similar numbering system as before is used, with reference numerals in the 400 series.

In this device the strip-form second channel 412 is retained within a housing 417, the housing being formed to provide an application window 402 for whole blood whilst providing a planar support for the second channel. The application window is afforded by means of a circular cup having a depending annular rim 421. The device also includes blood separation membrane 414 separated from the second channel 412 by an imperious membrane 416 in which a suitable gap 415 is provided. Blood separation membrane 414 is in flow contact with a further porous channel 440 which is provided as a waste overflow means.

The device includes a part 410 of the liquid flow strip, which is compressed to reduce the pore size therein and thereby provide a first channel, of higher capillarity than the abutting second channel 412, similar in function and operation to the separate piece of material 310 used in the device of FIG. 6, but more amenable to simple reliable production owing to the fact that the first and second channels are now formed integrally as two parts of a common piece of porous material. As FIG. 7 shows, the compressed first channel 410 can conveniently be formed by the action of enclosing the liquid transfer device within its housing 417. As the housing is assembled, the annular rim 421 of the application window forces the blood separation membrane 414 against the underlying porous material, compressing the latter material to form a zone of relatively high capillarity, the so-called first channel 410, in fluid contact with the separation membrane 414 by way of an interface 420. Once assembled, the device holds the second and third channels in clamped engagement whilst ensuring the application window 402 accesses the separation membrane in the vicinity of the interface region. Alternatively, it is possible to compress the material to form channel 410 before assembly of the device in order to avoid unduly stressing the housing. This latter practice also avoids the risk of unwanted excessive compression of part of the separation membrane 414, which can reduce the permeabililty of the membrane.

In use, the device is employed and operates in a similar manner to that of FIG. 6. with the compressed material of the first channel 410 retaining and defining the volume of applied sample plasma, until liquid diluent flowing through the second channel 412 wets this lower capillarity material and so entrains the sample volume. Appropriate materials for the device of FIG. 7 have been found to be Whatman 1001917 paper to provide channel 412, AP25 to provide waste channel 440, PS21 to provide separation membrane 414, and thin (0.1 mm) plastics film with an appropriate cutout 415 to provide impervious membrane 416. It will be appreciated that this device provides a porous flow device whose assembly automatically provides sample application means and sample definition means without the need for complex design or construction procedures.

An alternative practical form of this device shown in FIGS. 8a and 8b, which also provides a compressed sample volume definition zone, employs an elongate compression member. The advantage of such a member over that of the device of FIG. 7 is that more uniform compression of the first channel can readily be realised.

FIG. 8a shows the device in front view, whilst FIG. 8b provides a cross section along line X—X. Once again, features equivalent or corresponding to those in previous embodiments have been given the same reference numerals, but in the 500 series. As FIG. 8b shows, the arrangement of material is similar to that of the device of FIG. 7. except that the compression is provided by a bar 521 pressed by the device housing or otherwise against the separation membrane 514 to compress a strip of the underlying porous material and so provide an elongate sample definition first channel 510 of higher capillarity than the surrounding liquid transfer second channel 512 to act as the volume definition zone.

In use of the device, sample of whole blood in an appropriate quantity is applied (region 523) to the separation membrane 514. As in previously-described embodiments, this quantity is sufficient to provide enough plasma to pass to the volume definition zone 510, whilst not saturating the separation membrane. In practical tests, it was found that a constant plasma volume could be defined substantially irrespective of the volumes of applied whole blood sample throughout a range from 10 $\mu$l to 30 $\mu$l.

The device is also shown with a band of colloidal gold 550 between the liquid diluent application end of the second channel 512 and the sample volume definition zone 510, the gold being able to conjugate to an antigen specific to the antibody of interest and being able to migrate through the porous channel in the presence of liquid diluent 536. In a manner similar to that described in respect of the device of FIG. 7, liquid diluent is applied at one end 526 of second channel 512 from a reservoir 534. The diluent flows along the second channel, entraining first the gold 540 and then the defined plasma sample volume in the first channel 510. The serum and gold mixture then flows on through channel 512 to downstream reagent sites where analysis can take place.

Figure 9:
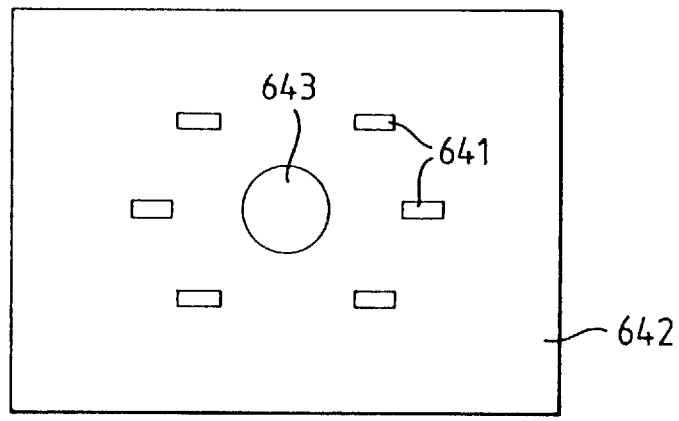

The above-described manner of forming a compressed zone to provide a sample definition volume first channel, by way of a member applying force on a part of a porous strip, has been found by the inventor to be applicable in a variety of liquid transfer devices where sample volume definition is required. It is also possible to form a compressed zone by applying an equal force on opposite sides of a portion of a porous strip, and experiments have shown that by applying two elongate compression members, such as two bars, one on each side of the strip, more uniform compression across the thickness of the strip can be achieved without requiring any additional compressive force. It is also possible to use the compression technique to form multiple sample volumes from a single sample. FIG. 9 illustrates one embodiment of this concept, where multiple 'pinch sites' 641 (in this case six in number) are realised in porous strip 642 by applying compressive force in an appropriate manner at those sites. When sample is applied, for example by way of a blood separation membrane, through an impervious mask, defined sample volumes are retained in the six compressed zones and multiple tests can then be simultaneously carried out on these samples by liquid transport techniques. It is desirable to arrange the pinch sites 641 equidistant from the site 643 at which the sample is to be applied to the separation membrane, to ensure that particular ones of the sites are not filled preferentially.

In the case of sample volume definition devices employing a blood separation membrane, it is important for a user to know whether or not enough plasma has arrived at the first channel volume definition zone. Present devices may provide means to indicate whether sufficient whole blood has been applied, but this is no indicator of plasma volume as the haematocrit of blood will vary between samples.

Figure 10:
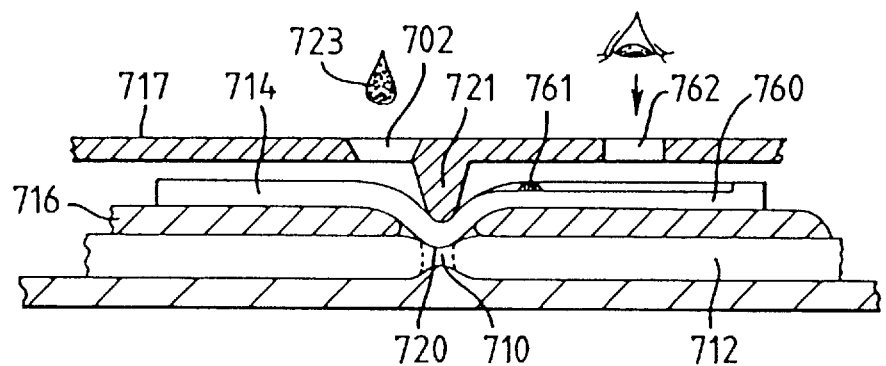

The invention additionally envisages means by which the sufficiency of this sample volume can be indicated, and a device incorporating such means is shown in FIG. 10. Once again the same reference numerals are used to indicate features similar to those used in respect of previously described embodiments, but this time in the 700 series. A blood separation membrane 714 is used, held in contact with first channel 710 by means of compression member 721 which is part of housing 717. The membrane itself is compressed, prior to device assembly, in an elongated region 760 (for example by means of a compression bar) extending from the vicinity of the interface region as shown. A line of dye 761 is provided on the top surface of the compressed region of the separator membrane, whilst the housing features an indicator window 762 in line with the compressed region 760 on the other side of the dye site from the interface 720.

The compressed region 760 provides a part of the separation membrane of high capillarity which will form a preferential flow path for liquid. In use, whole blood 723 is applied by way of application window 702 to the top surface of the separator membrane 714. When sufficient plasma has passed through to the collector side of the separation membrane to fill the first channel 710 with a defined volume, plasma will also be drawn into the compressed region 760. This plasma flow will entrain the dye indicator and, if present in sufficient quantity, will transport it past the indicator window 762. A user will thereby be able to see whether sufficient plasma has passed through the separator membrane, by looking for the dye stain visible through indicator window 762. If the dye stain does not appear in the window 762, further whole blood can be added at the application window 702.

As mentioned earlier in this description, saturation of porous material, whether localised or otherwise, allows liquid to flow from relatively high to relatively low capillarity material. It has been found that, in devices of the type described above, application of an amount of sample greatly in excess of that needed to provide the required sample volume plasma in the first channel can lead to localised saturation of the separation membrane at the interface region with the first channel, even if the volume of applied sample is insufficient to fill the entire separation membrane. This effect can in turn lead to unwanted saturation of the first channel and hence to poor sample volume definition as plasma progresses beyond the boundary between the first and second channels. Investigation with currently available blood separation membranes suggests that this is due to the fact that, when a large volume of blood is initially applied, red blood cells can begin to clog the membrane. This effect further exaggerates the reduction in the speed of progress of the blood as the wicking front spreads out towards the excess sample region of the membrane.

Figure 11:
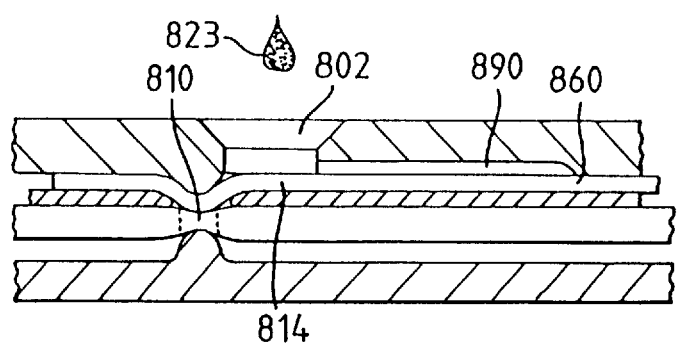

Further laboratory testing has indicated that these devices can be improved by ensuring that excess applied sample is effectively and rapidly passed to parts of the separation membrane distant from the interface region with the first channel. This can be accomplished by the provision of a small bore tubular capillary flow channel connecting the blood application site with the excess sample receiving portion of the separation membrane. This channel can be provided by means of appropriate shaping of the device housing in the vicinity of the sample application window (see reference 702 in FIG. 10), and a convenient shaping for this purpose involves a bore of rectangular cross-section forming a recess in the otherwise planar surface of the inside of the top portion of the housing such that, when the device is assembled, the said top portion contacts the separation membrane leaving only the tubular capillary flow channel directly connecting the sample application window with the excess sample receiving portion of the separation membrane. Such a device is illustrated in FIG. 11.

When blood sample 823 is applied by way of the application window 802 in a relatively small volume, it is absorbed by the separation membrane 814 and a defined volume of plasma passes into and is held by the first channel 810. If, instead, a large volume of blood is applied, it cannot be readily absorbed by the separation membrane for the reasons explained above. With the incorporation of a capillary flow channel 890 leading from the blood application site, excess blood can rapidly flow down this channel and be readily absorbed into a dry portion 860 of separation membrane 814. In a simple experiment on such a device, 30 µL of blood took about 7 seconds to be absorbed into the separation membrane when a capillary channel was present, and about 70 seconds in the absence of such a channel. Such a channel can therefore act to assist in controlling the volume of plasma transferred to the first channel. Additionally, such a channel can serve as an indicator of applied sample volume and, to this end, a transparent section can be provided in the housing of the device to enable a user to visualise at least a part of the tubular capillary channel 890 to see to what extent it has been filled by the applied whole blood sample.

It will be appreciated from the above examples that the devices concerned are accordingly simple and inexpensive to manufacture and, since no complex mechanical apparatus of procedure is required, are suitable for use by unskilled personnel.

It is to be noted that devices of the invention are readily adaptable to existing capillary flow strip devices, including multilayer and multichannel formats.

It is to be understood that the scope of the present invention is not to be limited to the specific embodiments described above. The invention may take forms within the scope of the accompanying claims other than those particularly described.

I claim:

1. A liquid transfer device for controlling liquid flow, comprising:
    first, second and third capillary flow channels, a fluid impermeable support mounting said second and third channels in spaced apart relationship, and said first channel being positioned overlying said second and third channels to define a first interface region between the first and second channels and a second interface region between the first and third channels,
    said first channel defining a volume definition zone for a first liquid to be applied, said volume definition zone being in fluid connection with said second channel by way of the interface region,
    said first channel defining a means for receiving excess first liquid spaced from said second and third channels in fluid connection with the volume definition zone and in fluid connection with said second channel only via said first channel,
    wherein said third channel is arranged for direct application of a second liquid,
    wherein said first channel has a higher capillarity than that of said second and third channels, and wherein said first, second and third channels with the first and second interface regions provide an ongoing liquid flowpath from a region of application of the second liquid, through the interface regions, to a downstream region, such that the second liquid is able to entrain first liquid in the volume definition zone and carry it to the downstream region.

2. A liquid transfer device for controlling liquid flow, comprising first, second and third capillary flow channels, said first and second channels being in abutment over a first interface region and said first and third channels over an abutment over a second interface region;
    said first channel defining a volume definition zone for a first liquid to be applied, the volume definition zone being in fluid connection with said second channel by way of the first interface region,
    means for receiving excess first liquid, in fluid connection with the volume definition zone and in fluid connection with said second channel only via said first channel,
    wherein said third channel is arranged for direct application of a second liquid,
    wherein said first channel has a high capillarity than that of said second and third channels, and wherein said first, second and third channels with the first and second interface regions provide an ongoing liquid flowpath from a region, such that the second liquid is able to entrain first liquid in the volume definition zone and carry it to the downstream region.

3. A liquid transfer device for controlling liquid flow, comprising:
    first and second capillary flow channels, said first and second channels being in mutual abutment over an interface region,
    said first channel defining a volume definition zone for a first liquid to be applied, the volume definition zone being in fluid connection with said second channel by way of the interface region,
    means for receiving excess first liquid, in fluid connection with the volume definition zone and in fluid connection with said second channel only via said first channel,
    wherein said second channel is arranged for direct application of a second liquid,
    wherein said first channel has a higher capillarity than that of said second channel, and wherein said second channel provides an ongoing liquid flowpath from a region of application of the second liquid, past the interface region, to a second channel downstream region, such that the second liquid is able to entrain first liquid in the volume definition zone and carry it to said second channel downstream region.

4. A liquid transfer device for controlling liquid flow, comprising first, second and third capillary flow channels, said first and second channels being in mutual abutment over an interface region wherein:
    said first channel defining a volume definition zone for a first liquid to be applied, the volume definition zone being in fluid connection with said second channel by way of the interface region,
    means defined by the third channel for receiving excess first liquid, in fluid connection with the volume definition zone and in fluid connection with said second channel only via the first channel,
    wherein said second channel is arranged for direct application of a second liquid,
    wherein said first channel has a high capillarity than that of said second channel, and wherein said first and second channels provide an ongoing liquid flowpath from a region of application of the second liquid, past the interface region, to a second channel downstream region, such that the second liquid is able to entrain first liquid in the volume definition zone and carry it to said second channel downstream region.

5. A device according to claim 3, wherein said means for receiving excess first liquid is a part of said first channel distant from said volume definition zone.

6. A device according to claim 4, wherein said third channel comprises means for introducing first liquid to said first channel.

7. A device according to claim 6, wherein said third channel comprises means for separating and retaining selected matter.

8. A device according to claim 7, wherein said third channel is a blood separation membrane for retaining red blood cells contained in whole blood whilst allowing passage of blood plasma.

9. A device according to claim 1, wherein the difference in capillarity between channels is obtained by forming the channels from materials having differing pore sizes and/or wetting characteristics.

10. A device according to claim 4, wherein the difference in capillarity between channels is obtained by modifying the capillarity of at least one channel by compressing or by selectively removing material.

11. A device according to claim 10, wherein the device includes a compression member to selectively compress capillary flow material thereby to form said first channel.

12. A device according to claim 11, comprising a housing containing said respective flow channels, the compression member forming part of the housing.

13. A device according to claim 12, wherein the housing is provided with first liquid application means associated with the compression member.

14. A device according to claim 10, wherein material is compressed in a number of discreet areas to create multiple volume definition zones.

15. A device according to claim 10, wherein opposed like compression members are provided on opposite sides of the channel.

16. A device according to claim 13, wherein the compression member is of elongate form for application to the capillary material to form a volume definition zone of elongate form.

17. A device according to claim 4, wherein said third channel is provided so as to overlie and engage said first channel on the opposite side thereof to said second channel.

18. A device according to claim 1, wherein said second and third channels are substantially coplanar and are bridged by said first channel which has a portion extending away from the volume definition zone to provide said means for receiving excess first liquid.

19. A device according to claim 4, comprising indicator means for giving an indication to a user whether or not sufficient first liquid has been applied to the volume definition zone.

20. A device according to claim 19, wherein the indicator means comprises a compressed region of one of the channels provided with a visible marker dye able to be entrained in liquid flow.

21. A device according to claim 4, comprising a tubular capillary flow channel in fluid connection with said means for receiving excess first liquid, to provide a flow path for such excess.

* * * * *